(12) United States Patent
Abitbol

(10) Patent No.: US 6,786,602 B2
(45) Date of Patent: Sep. 7, 2004

(54) ABERRATION CORRECTION SPECTACLE LENS

(76) Inventor: Marc Abitbol, 5/3 Bagio Street, Jerusalem (IL)

( * ) Notice: Subject to any disclaimer, the term of this patent is extended or adjusted under 35 U.S.C. 154(b) by 126 days.

(21) Appl. No.: 10/159,167

(22) Filed: May 31, 2002

(65) Prior Publication Data

US 2002/0196412 A1 Dec. 26, 2002

(30) Foreign Application Priority Data

May 31, 2001 (IL) ................................................ 143503

(51) Int. Cl.[7] .............................. A61B 3/00; A61B 3/10
(52) U.S. Cl. ....................... 351/246; 351/205; 351/161; 600/5
(58) Field of Search ................................ 351/200, 205, 351/206, 211–216, 219, 221, 246, 227, 247, 41, 159, 160 R; 600/558; 606/4, 5; 607/88, 8; 604/20

(56) References Cited

U.S. PATENT DOCUMENTS

| | | | |
|---|---|---|---|
| 4,957,369 A | | 9/1990 | Antonsson |
| 5,220,359 A | | 6/1993 | Roffman |
| 5,512,220 A | * | 4/1996 | Roffman et al. ............. 264/2.5 |
| 5,691,799 A | | 11/1997 | Ramachandran |
| 5,777,716 A | * | 7/1998 | Miura ......................... 351/169 |
| 5,777,719 A | | 7/1998 | Williams et al. |
| 5,926,247 A | | 7/1999 | Kimura |
| 5,949,521 A | | 9/1999 | Williams et al. |
| 5,980,040 A | * | 11/1999 | Xu et al. ..................... 351/162 |
| 6,095,651 A | | 8/2000 | Williams et al. |
| 6,155,684 A | | 12/2000 | Bille et al. |
| 6,222,621 B1 | | 4/2001 | Taguchi |
| 6,233,049 B1 | | 5/2001 | Kondo et al. |
| 6,286,957 B1 | | 9/2001 | Livnat |
| 6,466,892 B2 | | 10/2002 | Fujii et al. |
| 6,499,843 B1 | * | 12/2002 | Cox et al. .................... 351/246 |
| 6,512,518 B2 | | 1/2003 | Dimsdale |
| 6,554,425 B1 | * | 4/2003 | Roffman et al. ............ 351/177 |
| 6,607,274 B2 | * | 8/2003 | Stantz et al. ................ 351/221 |
| 6,609,793 B2 | * | 8/2003 | Norrby et al. .............. 351/212 |
| 2002/0007176 A1 | * | 1/2002 | Campin et al. ................ 606/5 |
| 2002/0122153 A1 | * | 9/2002 | Morris et al. ............... 351/159 |

FOREIGN PATENT DOCUMENTS

WO    WO-00/75716 A1    12/2000

OTHER PUBLICATIONS

W.J. Smith, "Modern Optical Engineering", Chapter 5 & 11, pp. 125–140, 366–383, published by SPIE Press, McGraw Hill, New York, 3rd edition, 2000.

* cited by examiner

Primary Examiner—Brian L. Casler
Assistant Examiner—John R Sanders

(57) ABSTRACT

A novel method for the design and construction of a spectacle lens for the correction of human vision, including the correction of high order aberrations. The lens enables the provision of super-normal vision using spectacles. Different lenses are described for use at a partial or a fuller field of view. The method applies corrective measures based on data obtained from high order wave front measurements of the subject's eye. According to one method, the Modulation Transfer Function (MTF) of the overall eye and lens optical system is optimized. According to another method, the optimization is performed on the wavefront of the overall eye and lens optical system. Both methods use weighted functions in the optimization procedure. This method of high order aberration correction is also applicable for the design of contact lenses and intra-ocular lenses, and for the execution of refractive eye surgery.

38 Claims, 6 Drawing Sheets

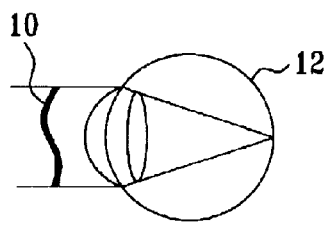
FIG. 1A
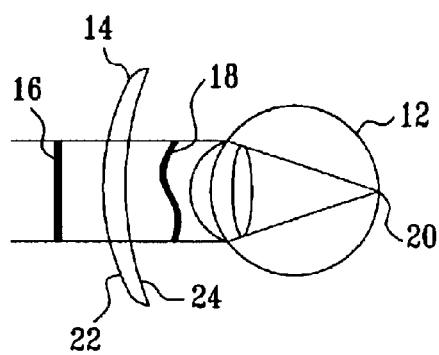
FIG. 1B
FIG. 2
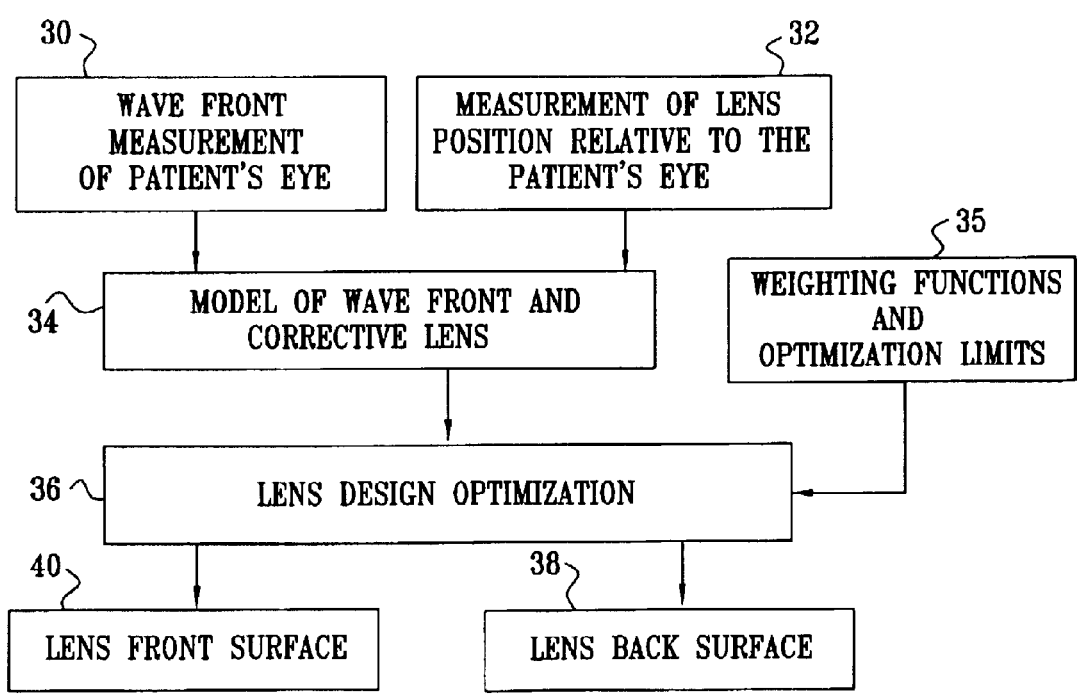

ABERRATION CORRECTION SPECTACLE LENS

FIELD OF THE INVENTION

The present invention relates to the field of vision correction, particularly to corrections achieved by means of spectacle lenses, contact lenses or intraocular lenses which include correction of high order aberrations.

BACKGROUND OF THE INVENTION

Currently performed optometric measurements for the determination of the specification of vision correction lenses generally measure aberrations of the type defocus and astigmatism, and to a lesser extent, also tilt. Common optometric devices for measuring defocus and astigmatism problems are the trial frame and the phoropter. Both devices rely on the subjective perception of the quality of sight perceived by the patient and therefore are referred to as subjective methods. Alternatively, an optical refractometer can be used for measuring defocus and astigmatism of the eye in an objective manner.

Aberrations such as tilt, defocus and astigmatism are considered low order aberrations. However, higher order aberrations, such as spherical aberration, coma and the even higher order aberrations, collectively known as irregular aberrations, are also present due to the imperfect optical properties of the human eye. The term "high order" or "higher order" aberrations, as used throughout this specification and as claimed, is meant to include all those aberrations besides the commonly corrected tilt, defocus and astigmatism aberrations. Furthermore, throughout this specification, and as claimed, the order by which aberrations are referred to are the orders of the wavefront aberrations, as expressed by their Zernike polynomial representation, rather than the order of ray aberrations. Under this convention, tilt, for instance is a first order aberration, defocus and astigmatism are second order aberrations, coma and coma-like aberrations are of third order, spherical and spherical-like aberrations are fourth order, and the above-mentioned irregular aberrations are those of fifth order and higher.

Once the diffraction limit of the eye's imaging capability has been exceeded, this occurring when the pupil size is typically larger than approximately 2 to 3 mm, the size of the minimum detail in the image projected onto the retina, and hence the ultimate visual acuity of the subject, becomes a function of how well the sum total of the aberrations present are corrected. If, in addition to the usually corrected power and astigmatism, higher order aberrations were also corrected, it would be possible to provide super-normal vision for the subject, with performance noticeably better than the commonly accepted optimum vision acuity, known as 20/20 vision. Since, however, correction of the low order aberrations generally improves vision to an acceptable level, little effort has historically been made to attempt to correct for the higher order aberrations present in the eye. Furthermore, even though low order aberration correction may provide acceptable visual acuity during the daytime or in well-lit rooms, under which conditions the pupil aperture is small, the level of low order correction may prove to be unacceptable at lower light levels, when the pupil aperture is larger and the level of aberrations increases.

In order to be able to correct higher order aberrations, the extent of these aberrations must be measured, and corrective measures then applied, such as the prescription of correction lenses or the performance of eye surgery. Different methods for measuring high order aberrations are described, for instance in U.S. Pat. No. 6,155,684, for "Method and Apparatus for Precompensating the Refractive Properties of the Human Eye with Adaptive Optical Feedback Control" to Bille et al.

A subjective method for measuring high order aberrations is described In Israel patent application No. 137,635 for "Apparatus for Interactive Optometry", filed by the applicants of the present application.

Recent developments in the field of high order aberration correction for the human eye have, to date, only involved either corrective action such as laser surgery, or the use of contact lenses or intraocular lenses. Effective correction of higher order aberrations using spectacles has not hitherto been considered possible, since effective correction of such higher order aberrations is sensitive to the direction of passage of the light through the lens. In the case of spectacles, the optical axis of the spectacle lens and the optical axis of the eye may deviate from each other, both because of the natural rolling action of the eyeballs and also because of the limited accuracy with which the spectacles may be fixed relative to the wearer's eyes.

In the published PCT application in Patent Document WO 00/75716 for "Super Vision" to E. I. Gordon, there is described a method of correcting for spherical aberrations in human vision by means of an aspherical lens design, but the method does not utilize full wavefront measurement. In this document, it is stated specifically that the suggested solution is inadequate for use with spectacle lenses, since "because of deviations between the corneal vision axis and the axis of the lens, eye glass (spectacle) type corrections are not however feasible unless some means are used to fix the cornea relative to the spectacle lens."

In U.S. Pat. No. 5,220,359 to J. H. Roffman for "Lens Design Method and Resulting Aspheric Lens", there is described a solution for aberration correction in contact, intraocular, natural or spectacle lenses. However, the suggested solution is for aspherical lenses only, which are rotationally symmetric. Furthermore, the method is a subjective method of substituting aspheric lenses until the optimum subjective correction is achieved, and does not involve a complete wavefront measurement.

Contact lenses and intraocular lenses, however, being more or less fixed relative to the eyes, are not considered to suffer from the above-mentioned disadvantage of spectacle lenses. In U.S. Pat. Nos. 5,777,719, 5,949,521 and 6,095,651, all for "Method and Apparatus for Improving Vision and the Resolution of Retinal Images" to D. R. Williams et al. (each a continuation of the previous), there are described methods of providing correction data of higher order aberrations for use in the manufacture of contact lenses and intraocular lenses, as illustrated in FIG. 1 of each of these patents. Very sparse enabling details are given, however, of how to apply the measurements obtained in the design of contact or intraocular lenses.

The majority of sight correction is still, however, currently achieved by the use of spectacles, this probably being the least expensive, most risk-free and most convenient method of sight correction. There therefore exists an important need for the provision also of spectacle lenses corrected for higher order aberrations.

The disclosures of each of the publications mentioned in this section, and in other sections of this specification, are hereby incorporated by reference, each in its entirety.

SUMMARY OF THE INVENTION

The present invention seeks to provide a new spectacle lens for the correction of human vision, including the correction of high order aberrations, and a method for constructing such a lens. The present invention thus enables the provision of super normal vision using spectacles. Different lenses are described for use at a partial or a fuller field of view (FoV). The method applies corrective measures based on data obtained from high order wave front measurements. Although the method of the present invention is described in this specification using its implementation in the prescription of spectacle lenses as a preferred embodiment to illustrate the method, it is to be understood that it may also be implemented with any other vision corrective measures such as contact lenses, intraocular lenses or even in refractive eye surgery.

As opposed to prior art methods of correcting high order aberrations in vision, using real-time wavefront measurements and corrective adaptive optics, the present invention achieves the correction by means of a suitably constructed fixed lens.

When customizing a spectacle lens to correct wave front aberrations, a natural solution would be to design a lens that would fully correct the wave front, thus creating an emetropic lens-eye system. Such a solution would indeed be practical if the eye and corrective spectacle lens were a deterministic fixed system. However, since the spectacles and eye are capable of mutual movement, both in position and angular alignment, this is not the case, and this simple solution, although optimized for one predefined relative position, is not robust to the real life situation of relative movement of eye and spectacles, resulting in degradation in vision.

Contact lenses designed to provide high order aberration correction, such as those described in the above-mentioned Williams et al. patents, have to be accurately aligned on the eye, both laterally and rotationally, in order to successfully provide high order vision correction, and maintaining such alignment is not a trivial task. If the same design criteria used for such contact lenses were to be applied for the construction of spectacle lenses with higher order aberration correction, the effect of tilt of the eye would significantly degrade the correction. The accurate alignment and positioning of spectacles, on the other hand, is a well known problem encountered with any non-rotationally symmetric lenses, such as cylindrical lenses, bifocals, multifocals or any of the modern progressive lens designs. Many different types of such lenses are widely and successfully used in spectacles, despite the alignment and position variation which can occur with spectacles.

There is thus provided, according to a preferred embodiment of the present invention, spectacle lenses which correct high order aberrations of the eye either for a full field of view or for a partial field of view. The embodiment for higher order correction for the full field of view is enabled by adopting a compromise correction, which is less than the optimum correction possible when the lens optical axis and the optical axis of the eye coincide, but which nevertheless provides an improvement over hitherto corrected low order aberrations in spectacle lenses. For the partial field of view embodiment, an optimum correction is performed over a limited paraxial region of the lens, and the well-known second order corrections are applied outside of this partial field of view.

According to both of these embodiments, super normal vision is provided to the user when the lens optical axis and the optical axis of the eye coincide. When there is deviation of the two axes, such as when the user does not look directly through the optical axis of the lens, or when the spectacles are being worn slightly misaligned in relation to the wearer's eyes, the lens designed according to these preferred embodiments of the present invention, provides vision quality reduced in comparison with optimal super vision ability, but the reduction in performance is sufficiently small that 20/20 vision or better is still maintained.

Lenses constructed according to preferred embodiments of the present invention, thus allow the user to experience super normal vision without undue difficulties when looking straight forward, and at the same time, significant tilt of the eye does not degrade the acuity of vision experienced compared to normal 20/20 vision. For large angles of tilt, it is usually more comfortable physically to tilt the head in the preferred direction. Thus, for the field of view generally used, these lenses thus provide significantly better vision correction than conventional prior art spectacle lenses can provide. Optimal use of spectacles incorporating lenses according to the present invention, is an easy-to-learn task, not dissimilar to that encountered in learning to use bifocal, multifocal or progressive lenses.

According to another preferred embodiment of the present invention, the spectacle lens is optimally corrected for higher order aberrations in the wearer's eyesight only over the central portion of the lens, typically within ±1° of its optical axis. Outside of this field of view, no correction beyond the conventional correction for power and astigmatism is attempted. The resulting lens thus provides super normal vision when the center of the lens is being used, and off axis, the performance tapers to that of conventional 20/20 correction.

Two preferred methods are suggested, according to different embodiments of the present invention, by which the corrective lens is designed in order to optimize the vision performance for acceptable values of the field of view and relative axial deviation between the eye and lens optical systems.

In a first preferred method the Modulation Transfer Function (MTF) of the overall eye and lens optical system is optimized. The MTF is commonly used to evaluate the performance of an optical imaging system, and specifically, the quality of the visual acuity achieved using the system. The MTF graph of the overall eye and lens system may thus be used to evaluate the performance of a corrective lens design, by optimizing the total summed MTF values for best overall performance over the range of use desired.

The major factors that influence the MTF value of this eye/lens system are spatial frequency, the angle of transit of the light, within the field of view, through an axially aligned eye and the tilt angle of the eye with respect to the lens. For the sake of simplicity, the latter two angles are termed and claimed as "vision angles" in this application. According to a preferred embodiment of this method, the effect of these three factors is taken into account, by implementing a weight function in the MTF optimization process. Each value of the MTF calculated is given a different weight, that is dependent on the spatial frequency, the angle in the field of view and the tilt angle of the eye used for that particular MTF calculation, according to predefined criteria dependent on subjective conditions and on the extent of correction sought. Thus, for example, the central field of view (the fovea) is given a significantly bigger weight than the outer field of view, since the visual acuity of the natural eye degrades so strongly in the outer field, that in general, only paraxial vision is used for high-definition sight. Furthermore, the MTF is calculated within a set of limited boundaries that are considered to be relevant for normal human vision, meaning a maximum defined resolvable spatial frequency, a maximum defined field of view and a maximum eye tilt angle.

After determining the weighting function and boundaries for performing the calculations, the lens surfaces are optimized to give an overall best MTF performance within the predefined boundaries and limitations applied to the correction required, taking into account the total MTF values and the related weights for the spatial frequencies, the FoV angles and the tilt angles.

According to the second preferred method, optimization is performed on the wavefront of the overall eye and lens optical system. After determining the weight functions and boundaries to be used for the angle in the field of view and for the tilt angle of the eye, the correction lens surfaces are optimized to give the overall minimum wave front aberrations, preferably defined by minimum RMS deviation from a plane wave of the wavefront, taking into account the related weights for the various FoV and tilt angles. If measurements of the wavefront at different field of view angles are not available, than the optimization is done only for the various tilt angles. The wavefront RMS for a specific tilt angle is the RMS of the resulting wavefront, when the measured wavefront is transmitted through the corrective lens at the specific tilt angle. The optimized lens is then calculated such as to minimize the total value of all RMS values at various tilt angles, including the effects of their relevant weights.

According to both of the above preferred methods, the inputs used for the lens design include wavefront measurement of the patient's eye and measurement of the correction lens position relative to the patient's eye.

The design of the lens, according to various preferred embodiments of the present invention, consists of at least some of the following steps:

i. A wavefront measurement of the eye is performed. Such a measurement can be attained by a wave front analyzer, such as those described in the above-mentioned U.S. Pat. Nos. 6,155,684 or 6,095,651. The output of such a wavefront measurement can be either an X-Y-Z co-ordinate plot of the wavefront surface or a polynomial (Zernike, Taylor or another) describing the aberrations measured.

ii. The wavefront measured is automatically transformed by software into a corrective lens design, which consists of a back surface and a front surface. One surface may preferably be spherical and/or cylindrical and is operative to correct lower order defocus and astigmatism aberrations. The second surface may preferably be any X-Y-Z defined surface, and is operative to correct the higher order aberrations.

iii. Alternatively and preferably, any combination of two surfaces may be used which results in correction of the wave front.

iv. The design described in sections ii or iii above can be calculated such that for a specific predetermined position of a lens relative to the inspected eye, the wavefront is distorted by the lens in such a manner that the aberrations in the eye's optical system corrects the distortion to produce an exact image on the retina, undistorted by the aberrations of the eye. Thus, the total lens-eye system will behave as a perfectly corrected optical system.

v. A solution according to a preferred embodiment of the present invention is a design that gives an optimized, but not perfectly corrected solution over a wide field of view. This optimized solution is defined as a lens design, which, together with the eye, has a total residual aberration such that when calculated across a defined field of view around the eye/lens optical axis, it gives the minimal standard deviation of distortion from zero.

vi. Alternatively and preferably, the optimized solution is defined as a lens design, which, together with the eye, has a total residual aberration such that when calculated across a defined range of angles of tilt of the optical axis of the eye with respect to the lens optical axis, it gives the minimal standard deviation of distortion from zero.

vii. Even more preferably, the optimized solution is defined as a lens design, which, together with the eye, has a total residual aberration such that when calculated across a defined field of view around the eye/lens optical axis, and across a defined range of angles of tilt of the optical axis of the eye with respect to the lens optical axis, it gives the minimal standard deviation of distortion from zero.

viii. Another preferred solution consists of the above high order corrections performed only for a limited area around the optical axis. Over the remainder of the lens area, correction is preferably made only for lower order aberrations (defocus and cylinder). A smooth transition is applied between the two sections.

ix. Any of the above-mentioned preferred designs, after calculation by a suitable program, may be transformed into a formatted data file for outputting directly to a lens manufacturing machine. The lens is then manufactured according to the prescribed data file. The manufacturing process needs to be such that the unique non-symmetric correction surface may be easily manufactured (CNC or similar).

x. Software is provided for conversion of the wave front measurement data into a data file for manufacturing of a corrective lens. The conversion is performed according to any of the methods mentioned above.

It is to be understood that the methods, according to the above-mentioned preferred embodiments of the present invention, which involve optimization of the correction lens for angular ranges of both tilt and field of view are relevant specifically for the optimization of spectacle correction lenses. If one of the above-mentioned preferred methods is used for optimization of either contact or intraocular lenses, or for optimizing the parameters of a refractive surgical procedure on the eye, the optimization is only meaningfully performed over a range of angles of the field of view, since the lens is fixed relative to the eye, and there cannot therefore be any meaningful tilt.

Furthermore, when performing refractive surgery of the eye to correct the aberrations present therein, a common method used is to ablate the surface of the cornea to the desired shape using an excimer laser. The cornea is only one component of the ocular imaging system, which effectively consists of a number of optically operative elements, starting with the outermost refractive surface of the cornea, through the aqueous humor, the lens and the vitreous humor. The cornea supplies approximately two thirds of the eye's refractive power, and the lens most of the remainder. According to a preferred method of the present invention, in which optimization of optical parameters of the ocular imaging system is performed in preparation for refractive surgery, the only parameter in fact available for optimization is the accessible front surface of the cornea. The profile of the cornea can be accurately measured by means of corneal topography, to provide a starting value for the optimization procedure. The optimization procedure is preferably performed by adjusting the corneal front profile to reduce the aberrations present in the subject's vision over a predetermined range of angles of off-axis vision within a defined field of view of the subject's eye, and also optionally over a predetermined range of spatial frequencies.

There is also provided in accordance with another preferred embodiment of the present invention, a method of correcting aberrations in the vision of a subject, consisting of the steps of measuring the aberrations at an eye of the subject, providing a correction lens, and optimizing over a range of vision angles, parameters of the correction lens, such that the aberrations are minimized over the range.

The parameters of the lens may preferably consist of at least one of a first surface, a second surface, and a thickness, while the aberrations may preferably consist of high order aberrations.

Furthermore, the correction lens may be either a spectacle lens, a contact lens or an intraocular lens. For the case of a spectacle lens, the vision angles may be angles of tilt of the axis of the eye relative to the lens and/or angles of off-axis vision of the eye. For a contact lens or an intraocular lens, the vision angles may preferably be angles of off-axis vision of the eye.

In accordance with yet another preferred embodiment of the present invention, the method of optimization of the parameters of the lens as described above, may consist of the steps of calculating a first modulation transfer function of a combination of the lens and the eye for a given vision angle of the eye, varying the vision angle over a predefined range of angles, calculating new modulation transfer functions for each of a plurality of vision angles within the range of angles, performing a summation of the calculated modulation transfer functions, and varying the parameters of the lens to optimize the summation of the modulation transfer functions.

Furthermore, when the correction lens is a spectacle lens, the optimization of the parameters of the lens as described above, may preferably consist of the steps of calculating a first modulation transfer function of a combination of the lens and the eye for a given angle of tilt and a given angle of off-axis vision of the eye, varying at least one of the angle of tilt and the angle of off-axis vision over a predetermined range of angles, calculating new modulation transfer functions for the range of angles, performing a summation of the calculated modulation transfer functions, and varying the parameters of the lens to optimize the summation of the modulation transfer functions.

In the above described methods, the step of optimizing the parameters of the correction lens over a range of vision angles may preferably be performed over a predetermined range of spatial frequencies.

In addition, the above mentioned step of measuring the aberrations at an eye of the subject preferably consists of measuring a wavefront emitted from the subject's eye. The calculation of a modulation transfer function of the combination of the lens and the eye may preferably be performed by calculating the effect of the passage of the wavefront through the lens.

In accordance with yet more preferred embodiments of the present invention, the calculation of the modulation transfer function mentioned above, may also consist of the step of applying a predefined weighting to each of the new modulation transfer functions for each of the vision angles before the summation of the calculated modulation transfer functions is performed. This predefined weighting may preferably be a function of the angle of tilt of the axis of the eye relative to the lens, and/or of the angle of off-axis vision within a predefined field of view of the eye, depending on the case.

In accordance with still more preferred embodiments of the present invention, in the methods described above where the method of measuring aberrations at an eye of a subject consists of measuring a wavefront emitted from the subject's eye, the optimization of the parameters of the lens may preferably consist of the steps of calculating the deviation of the wavefront from a plane wavefront after passage through the combination of the lens and the eye, for a given vision angle of the eye, varying the vision angle over a predefined range of angles, calculating a new deviation of the wavefront for each of a plurality of vision angles within the range of angles, summing the calculated deviations of the wavefront, and varying the parameters of the lens to minimize the sum of the deviations of the wavefront from a plane wavefront.

Alternatively and preferably, the optimization of the parameters of the lens may consist of the steps of calculating the deviation of the wavefront from a plane wavefront after passage through the combination of the lens and the eye, for a given angle of tilt and a given angle of off-axis vision of the eye, varying at least one of the angle of tilt and the angle of off-axis vision over a predetermined range of angles, calculating a new deviation of the wavefront for each of a plurality of vision angles within the range of angles, summing the calculated deviations of the wavefront, and varying the parameters of the lens to minimize the sum of the deviations of the wavefront from a plane wavefront.

In accordance with yet more preferred embodiments of the present invention, the calculation of the deviation of the wavefront from a plane wavefront after passage through the combination of the lens and the eye, as mentioned above, may also consist of the step of applying a predefined weighting to each of the deviations of the wavefront calculated for each of the vision angles before the summation of the calculated deviations is performed. This predefined weighting may preferably be a function of the angle of tilt of the axis of the eye relative to the lens, and/or of the angle of off-axis vision within a predefined field of view of the eye, depending on the case.

There is further provided in accordance with still another preferred embodiment of the present invention, a method of correcting aberrations in the vision of a subject, consisting of the steps of measuring the aberrations at an eye of the subject, measuring the profile of the front surface of the cornea of the eye, optimizing over a range of angles of off-axis vision within a predetermined field of view of the eye, the front surface of the cornea, such that the aberrations are minimized over the range, and performing refractive surgery on the eye such that the cornea acquires the optimized front surface.

In the above mentioned method, the optimization of the front surface of the cornea may preferably consist of the steps of calculating a first modulation transfer function of the eye with the front surface for a given angle of off-axis vision of the eye, varying the angle of off-axis vision over a predefined range of angles, calculating new modulation transfer functions for each of a plurality of angles of off-axis vision within the range of angles, performing a summation of the calculated modulation transfer functions, and varying the front surface of the cornea to optimize the summation of the modulation transfer functions.

Furthermore, the optimization of the front surface of the cornea over a range of angles of off-axis vision may be performed over a predetermined range of spatial frequencies.

Additionally and preferably, the method may also consist of the step of applying a predefined weighting to each of the new modulation transfer functions for each of the angles of off-axis vision before the summation of the calculated modulation transfer functions is performed. The predefined weighting may also be a function of the angle of off-axis vision within a predefined field of view of the eye.

In accordance with a further preferred embodiment of the present invention, the measuring of the aberrations at an eye of a subject mentioned above in connection with optimization for refractive surgery, may preferably consist of measuring a wavefront emitted from the subject's eye. In such a case, the optimization of the front surface of the cornea may consist of the steps of calculating the deviation of the wavefront from a plane wavefront after passage through the eye with the cornea front surface, for a given angle of off-axis vision of the eye, varying the angle of off-axis vision over a predetermined range of angles, calculating a new deviation of the wavefront for each of a plurality of vision angles within the range of angles, summing the calculated deviations of the wavefront, and varying the front surface of the cornea to minimize the sum of the deviations of the wavefront from a plane wavefront.

Furthermore, in any of the above-mentioned methods of correcting aberrations in the vision of a subject by refractive surgery, the aberrations may consist of high order aberrations.

Finally, there is provided in accordance with yet further preferred embodiments of the present invention, a lens for correction of aberrations in the vision of a subject, constructed by any of the methods mentioned above.

BRIEF DESCRIPTION OF THE DRAWINGS

The present invention will be understood and appreciated more fully from the following detailed description, taken in conjunction with the drawings in which:

FIGS. 1A and 1B are schematic views of the method whereby a spectacle lens, constructing and operative according to a preferred method of the present invention, corrects for higher order aberrations occurring in the user's eye. FIG. 1A schematically shows measurement of the aberrated wavefront from the eye, and FIG. 1B schematically shows how the lens corrects these aberrations;

FIG. 2 is a flowchart schematically describing the steps taken in constructing lenses according to a preferred embodiment of the present invention;

DETAILED DESCRIPTION OF PREFERRED EMBODIMENTS

Figure 3A:
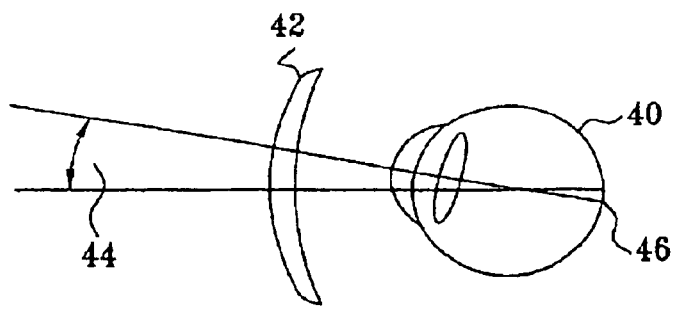
FIGS. 3A and 3B are schematic diagrams for illustrating respectively the use of the terms tilt and field of view, as used in preferred embodiments of the present invention.

Reference is now made to FIGS. 1A and 1B, which schematically illustrate the method whereby a spectacle lens, constructing and operative according to a preferred embodiment of a method of the present invention, corrects for aberrations occurring in the user's eye, including corrections of higher order aberrations.

In FIG. 1A is shown a measured wavefront 10 exiting the eye 12 of a subject. The wavefront is distorted because of the aberrations present in the eye, including higher order aberrations, and the object of the measurement step is to characterize these distortions. FIG. 1B is a schematic illustration of a lens 14, constructed according to a preferred embodiment of the present invention, located in front of the subject's eye 12. The lens 14 has a predetermined shape, such that a predetermined distortion is applied to a parallel undistorted wavefront 16 on traversing the lens. This predetermined distortion is such that when this wavefront 18 is imaged by the eye 12, the known measured aberrations of the eye, including higher order aberrations, exactly compensate for the applied predetermined distortion of the wavefront 18, and an undistorted image is focused onto the retina 20.

The lens 14 preferably has two surfaces, 22, 24, at least one of which is free-form, in order to enable the lens to compensate for the higher order aberrations of the eye.

Reference is now made to FIG. 2, which is a flowchart schematically describing the steps taken in constructing a lens according a preferred embodiment of the present invention. In step 30, the aberrations in the eye to be corrected are measured by means of wavefront analysis, as is known in the art. The output of this measurement is preferably in the form of a Zernike polynomial, describing the wavefront distortion measured in step 30. In step 32, the lens position and inclination relative to the patient's eye is measured. These measurements are necessary since the correcting lens and the eye to be corrected together form one optical imaging system to be optimized, and the inter-lens distance of such a system, for instance, is one of the parameters which determines performance. Preferably, the back vertex distance and the pantoscopic angle are the most important parameters required in step 32. In step 34, the measurements of the wavefront and lens position made in steps 30 and 32 respectively, are entered into a model including the distorted wavefront and an initial estimate for the precompensating correction lens, typically corrected for power, or power and astigmatism only. The weighted parameters used to define the boundaries and extent of the correction required are stored in step 35. Using these weighting parameters and correction boundary limits, in step 36, a lens design is optimized which corrects for the aberrations defined in the model used in step 34. This optimization can be preferably performed by an optical design software package as is known in the art, such as the Zemax program, manufactured by Focus Software Inc. of Tucson, Ariz., U.S.A., or by any other suitable optimization method. For a given lens material entered into the optimization program, the output of this lens design step is the shape and thickness of the lens, including the shapes of the first surface profile 40 and the second surface profile 38 of the lens. As is known in the art, one of these surfaces may preferably be spherical to correct defocus aberrations, with or without a cylindrical component to correct astigmatism. Use of such a toroidal shape for one surface provides convenience and compatibility with conventionally supplied lens shapes. The second surface may preferably be a free-form surface, computed to optimally compensate the aberrations, including higher order aberrations, measured in step 30. Alternatively and preferably, both surfaces may be free-form, and their combined refractive effect used to correct both the lower order and higher order aberrations.

Figure 3B:
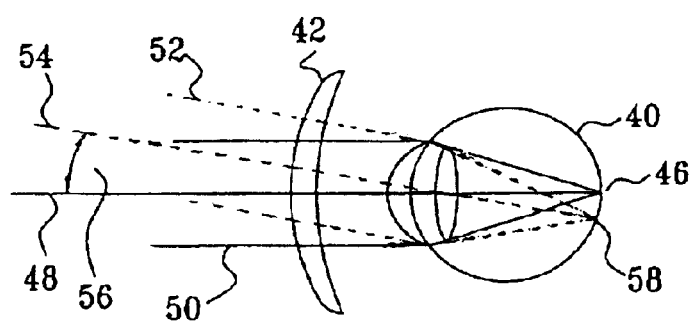

Reference is now made to FIGS. 3A and 3B, which are schematic diagrams for illustrating the use of the terms tilt and field of view. In FIG. 3A, there is shown a schematic eye 40, whose vision is corrected by means of a spectacle lens 42. The optical axis of the eye 40 is tilted with respect to the lens 42, such that the light from the object being viewed traverses the lens 42 at an angle from its optical axis. This angle is known as the tilt angle 44. Since the eye is tilted towards the direction of the object, the light is focused onto the fovea 46 of the retina, which is the center of sharpest vision.

In FIG. 3B, there is shown the same schematic eye 40 as in FIG. 3A, with its vision corrected by means of a spectacle lens 42. However, in this case, in order to illustrate the effect of differing fields of view on the subject's vision, the eye 40 is shown untilted with respect to the spectacle lens 42. The solid lines show the optical axis of the eye 48 and an incoming axial beam of light 50 being focused by the eye onto the fovea 46 of the retina. In contrast to this, the dotted lines show an incoming off-axis beam of light 52, whose central ray 54 makes an angle 56 with the optical axis of the eye which delineates the limit of the field of view. Because of the angle of the FoV, the off-axis beam is not focused onto the retina at the fovea 46, but at a spot 58 some distance from it.

The field of view in a typical normal subject extends to approximately a half solid angle, being slightly more than 180° in the horizontal direction, and slightly less in the vertical direction. However, it is well-known from the physiology of the eye, for instance in FIG. 5.2 on page 129 of the book entitled "Modern Optical Engineering" by W. J. Smith, published by SPIE Press, McGraw Hill, New York, 3$^{rd}$. edition, 2000, herewith incorporated by reference, that the visual acuity of the eye decays very rapidly as the retinal position of the image moves away from the fovea. Thus, for example, when the incoming light is at an angle of ±2° from the eye's optical axis, the visual acuity is only approximately 50% of its maximum foveal value, while for an angle of ±20°, the visual acuity is one order of magnitude less than its maximum foveal value. The subjective result of this phenomenon is that the field of view practically used by a typical healthy subject is generally limited to a very small angle, of the order of a degree or two in normal visual usage. For this reason, correction for aberrations over a wide field of view is not regarded as necessary, since only a narrow field of view is generally used.

Tilt, on the other hand, is a widely used movement in normal visual activity, and angles of tilt of 20°, and even more, are typically used before the muscular discomfort of holding the eyeball tilted makes it preferable for the subject to turn his head into the direction he is looking. For this reason, the angle of tilt should preferably be taken into account when optimizing the MTF of the lens/eye system for aberrational correction.

Figure 4A:
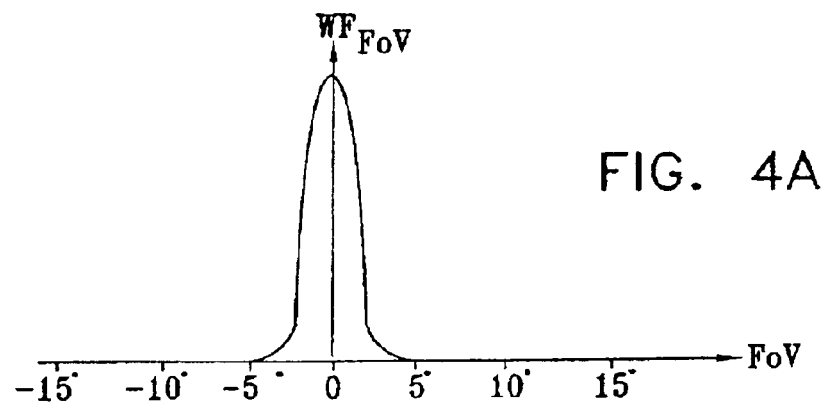
FIGS. 4A and 4B show typical graphs of weighting factors W used respectively for the field of view and tilt angles in weighting the MTF for the optimization procedure according to preferred embodiments of the present invention.
Figure 4B:
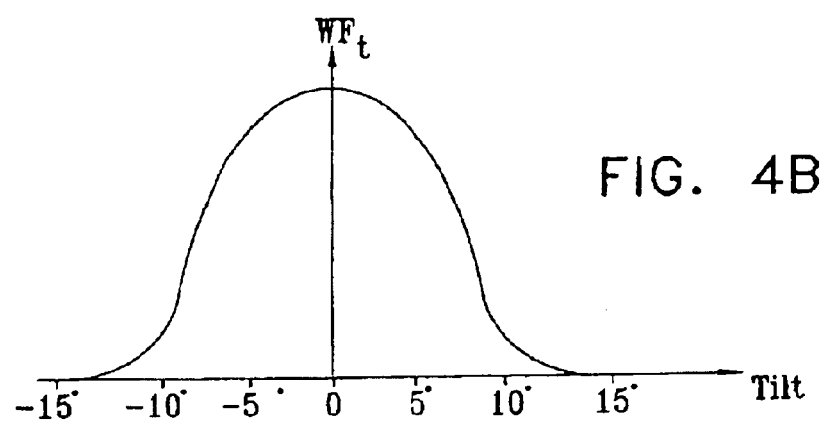

Weighting factors are applied to the possible ranges of angles of view and angles of tilt and the MTF for the tangential and sagittal fan of rays defined by the boundaries of vision to be corrected are calculated using the relevant weighting factor for each point calculated. Reference is now made to FIGS. 4A and 4B, which show typical graphs of weighting factors W used respectively for the field of view and tilt angles in weighting the MTF for the optimization procedure. Each graph shows the weighting used as a function of the specific parameter only. In FIG. 4A, since the field of view over which correction is required is limited, the preferred weighting curve used is sharp around the optical axis of the eye, and outside of this region, falls rapidly to zero. In FIG. 4B, on the other hand, is shown a preferred weighting curve used for tilt correction, having a wide top and a broad half-width, such that tilt over a wide range of angles is taken into account in optimizing the MTF of the eye/lens optical system. The exact shape of the weighting curves is selected according to a combination of the physiological effects of the parameter being weighted, and the subjective requirements of the correction desired. The angular extent of the weighting curves defines the boundaries of correction to be applied.

The MTF of the eye/lens system, for use according to a preferred method of optimization of the present invention, is given by the expression:

$$MTF = MTF[V, (\alpha_{FoV}), (\alpha_t)],$$

where:

V is the spatial frequency in cycles per mm;

$\alpha_{FoV}$ is the vectorial angle in the field of view; and $\alpha_t$ is the tilt angle.

It is understood that the angles are taken over the complete range in both azimuthal and vertical directions.

According to this first preferred method of the present invention, the lens parameters, such as the surface shapes, and the lens thickness, are optimized using a commercial optical design program, in order to maximize the total sum of the MTF of the eye/lens system, within the constraints of the boundaries and weightings given to the visual parameters, as described above. Alternatively and preferably, any other optimization method can be used besides commercial optical design software. This summation of MTF's can be expressed as:

$$\Sigma MTF[V, \alpha_{FoV}, \alpha_t] \cdot W[V, \alpha_{FoV}, \alpha_t]$$

where W is the predetermined weighting function as a function of the spatial frequency resolution; the field of view angle; and the tilt angle.

The spatial frequency may or may not be weighted depending on the method of subjectively specifying the value of the MTF in determining required system performance. Spectacle lenses for different subjective use may preferably be constructed emphasizing better low spatial frequency performance, or high spatial frequency performance, or neither, and a weighting factor applied or not applied accordingly.

The result of this optimization process is a spectacle lens which provides optimum correction of aberrations, including higher order aberrations, for the subject's eye over a predefined range of tilt angles and over a predefined field of view, and optionally over a predefined range of spatial frequencies. The lens according to this preferred embodiment of the present invention provides super vision over the range of tilts and field of view preselected. Though the level of visual acuity attained falls short of the maximum level possible with an optimized, purely axial correction, it is generally still significantly better than the level of visual acuity achievable with prior art lenses corrected for low order aberrations only, and also better than the level of visual acuity achievable overall with prior art lenses corrected for higher order aberrations but only for paraxial vision.

According to a second preferred embodiment of the present invention, the correction lens design is optimized, by means of an optical design program, such that the wavefront which exits the eye, after passing through the correction lens, has a minimum level of aberrational distortion departure from a plane wavefront. One preferred method of defining this minimum is by taking the RMS departure from a plane wavefront of the calculated wavefront at each point, and summing all of these RMS values for each optimization iteration, to achieve the minimum RMS deviation level. This ensures that the lens provides optimal correction of the aberrations of the eye, including high order aberrations. Like the first preferred embodiment, the optimization is performed taking into account the relative weighting factors and boundaries of the field of view and tilt angles, and the spatial frequency range over which optimum correction is to be achieved. Like the first embodiment, the major weighting is preferably applied to the tilt angle, such that the resulting lens design is that which shows optimal aberration correction, including high order aberrations, over the defined tilt angle range, and with minimal sensitivity to change of the tilt angle.

Figure 5A:
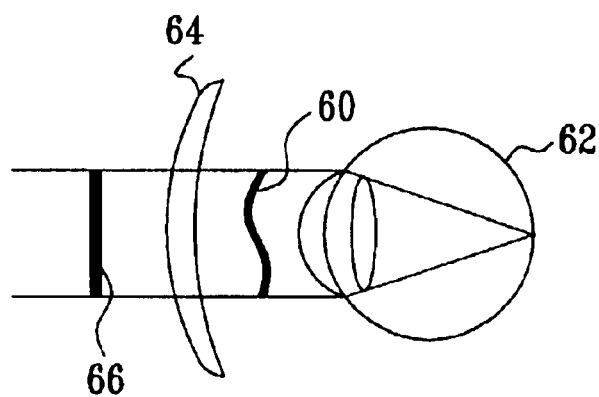
FIGS. 5A and 5B schematically illustrate the results of optimization processes according to preferred embodiments of the present invention, respectively for an on-axis imaging case, and for a case of the eye imaging at a tilt angle.
Figure 5B:
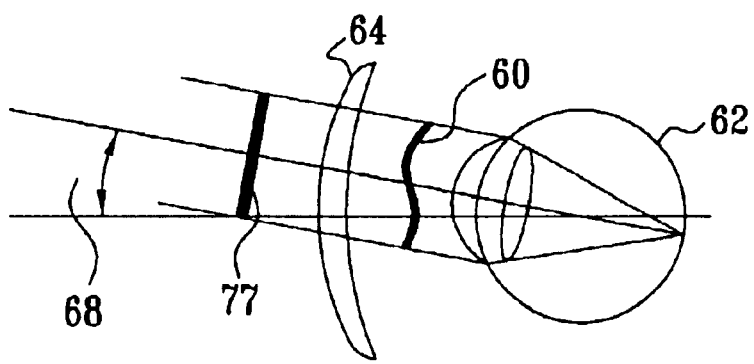

Reference is now made to FIGS. 5A and 5B, which schematically illustrate the result of the above optimization process for an on-axis imaging case, and for a case of the eye imaging at a tilt angle. In FIG. 5A, the measured wavefront 60 at the exit of the eye 62, distorted because of the inherent aberrations of the eye, is corrected by paraxial passage through a lens 64, constructed according to one of the preferred methods of the present invention, and the resulting wavefront measured in front of the lens is a corrected wavefront 66, as optimally close to an undistorted plane wave as the optimization procedure of the present invention has allowed.

In FIG. 5B, the eye 62 is tilted at an angle 68 to its natural straight-ahead position. The wavefront 60 measured on the eye's optical axis at its exit is identical to that measured for the case of FIG. 5A since the aberrations are, to a first order, independent of roll of the eye. The wavefront in this case passes through the correction lens non-axially, but the lens, constructed according to one of the preferred methods of the present invention, is such that the resulting wavefront measured in front of the lens is a corrected wavefront 70, as optimally close to an undistorted plane wave as the optimization procedure of the present invention has allowed. In general, the correction achieved at such a tilt angle is less than that achieved for the wavefront 66 in the straight-ahead case shown in FIG. 5A, but the correction is still sufficiently good that the level of visual acuity achieved is generally better than that achieved by prior art methods of correction only of low order aberrations. By alternative selection of the weighting factors used in the optimization procedure, optimum correction can be preferably achieved at angles other than for the straight-ahead orientation, if this is the desired performance required.

Reference is now made to FIGS. 6 to 10, which are plots of the modulation transfer function for images produced by a standard healthy eye, a myopic eye, an eye whose vision is corrected by means of a prior art spectacle lens, correcting for low order aberrations only, and an eye corrected by means of spectacle lenses constructed according to preferred embodiments of the present invention. It should be emphasized that the MTF curves plotted represent the performance of the optical imaging system only, and that retinal limitations will generally not enable achievement of the full acuity indicated by the MTF curves. The MTF curves are plotted for an eye having an entrance pupil of 3 mm, and for fields of view of up to 10°. The diffraction limit for these conditions is also plotted on each graph, as curve 71.

Figure 6:
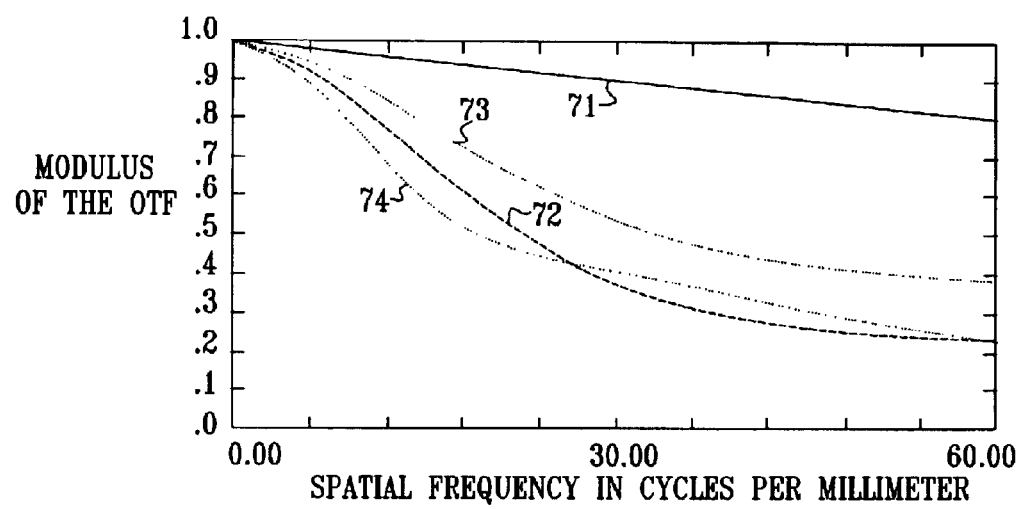
FIG. 6 shows plots of the modulation transfer function (MTF) for imaging produced by a standard healthy eye, having what is commonly termed 20/20 vision.

FIG. 6 is a set of MTF curves for a standard healthy eye, having what is commonly termed 20/20 vision. Curve 72 shows the MTF for on-axis vision down the center of the field of view. The MTF curves labeled 73 and 74 are those obtained at the limits of the field of view used in this optimization, namely ±10°.

Figure 7:
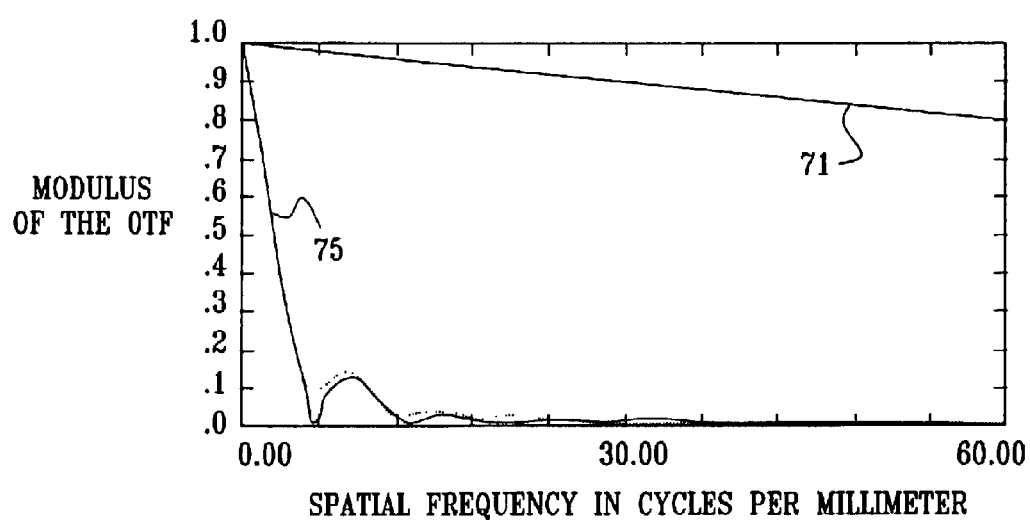
FIG. 7 shows plots of the MTF for imaging produced by a myopic eye.

In FIG. 7, there is shown a typical set of MTF curves 75 of a myopic eye. As is observed, the MTF is severely degraded from that of the standard eye shown in FIG. 6, even at very low spatial frequencies. Little difference is observed over different angles of field of view.

Figure 8:
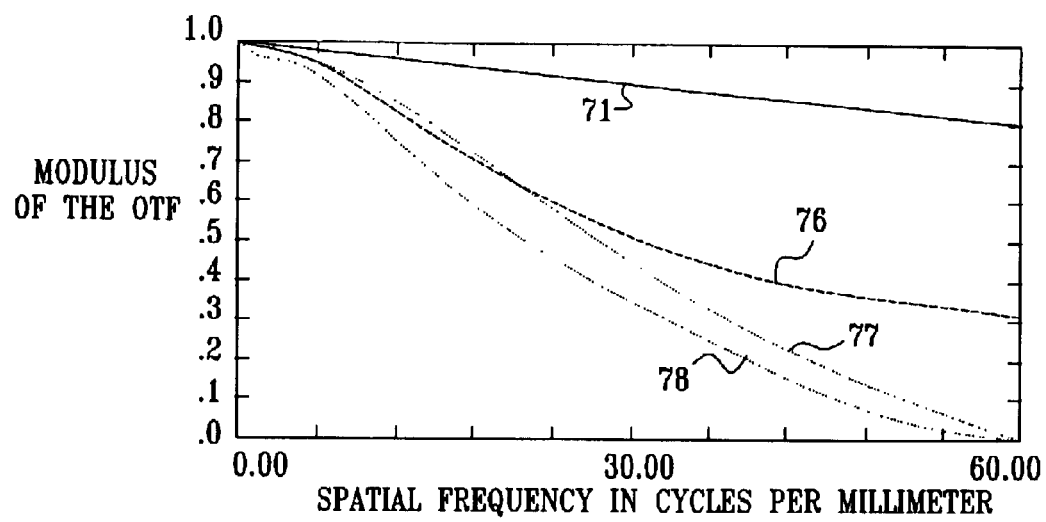
FIG. 8 shows plots of the MTF for imaging produced by an eye whose vision is corrected by means of a prior art spectacle lens, correcting for low order aberrations only.

The use of prior art spectacle lenses to correct for defocus and astigmatism only, is able to provide an MTF, as shown in FIG. 8, similar to that of the standard eye. Curve 76 shows the MTF at the center of the field of view, and curves 77 and 78 at the limits of the field of view used in this optimization, namely ±10°. As is observed, the correction at the center of the field of view is good, but it decays significantly off axis, especially at the higher spatial frequencies.

Figure 9:
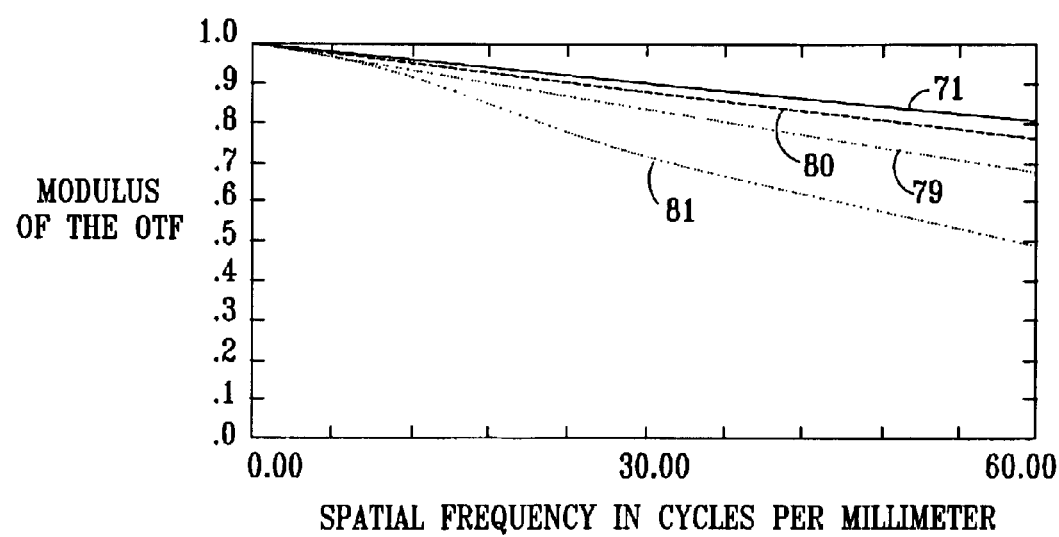
FIG. 9 shows plots of the MTF for imaging produced by an eye corrected by means of spectacle lenses constructed according to a preferred embodiment of the present invention, when the user looks through the lens axially.

Reference is now made to FIG. 9, which is an MTF plot of an eye, whose vision has been corrected by means of a spectacle lens constructed and operative according to a preferred embodiment of the present invention, to provide the optimum possible higher order aberration correction over a field of view of ±10°. The MTF for the central field of view is marked 80, and those at the extremities, 79 and 81.

As is observed, the MTF curves are significantly improved with respect to those obtained with the prior art lens, shown in FIG. 8, and even with respect to a healthy eye, such that an excellent level of super vision is achieved. It is found that an improvement of up to 300% is obtained in the MTF of the corrected visual image, and as is observed, the MTF curve is very close to that of the diffraction limit for that pupil size. In effect, such a level of improvement in visual acuity is not practically achievable, since due to the size of the photo-receptor spacing on the retina the retinal resolution limits optimum visual acuity to about 20/8. An important feature of the results shown in FIG. 9 is apparent in that the visual acuity at the edges of the allowed field of view shows only a slight fall off in performance from that on axis. The visual acuity achieved is seen to be still significantly better than that achieved with the prior art correction lens, or even with a standard healthy eye.

However, the optimum correction shown in FIG. 9 is only achieved for on-axis vision, when the eye is centralized with respect to the optical axis of the corrected lens, both laterally and angularly, and the MTF is optimized for the full field of view chosen, ±10°. If the eye and lens are mutually tilted such that there is an angular deviation between these two optical axes, then the image quality decays in comparison with the on-axis con.

Figure 10:
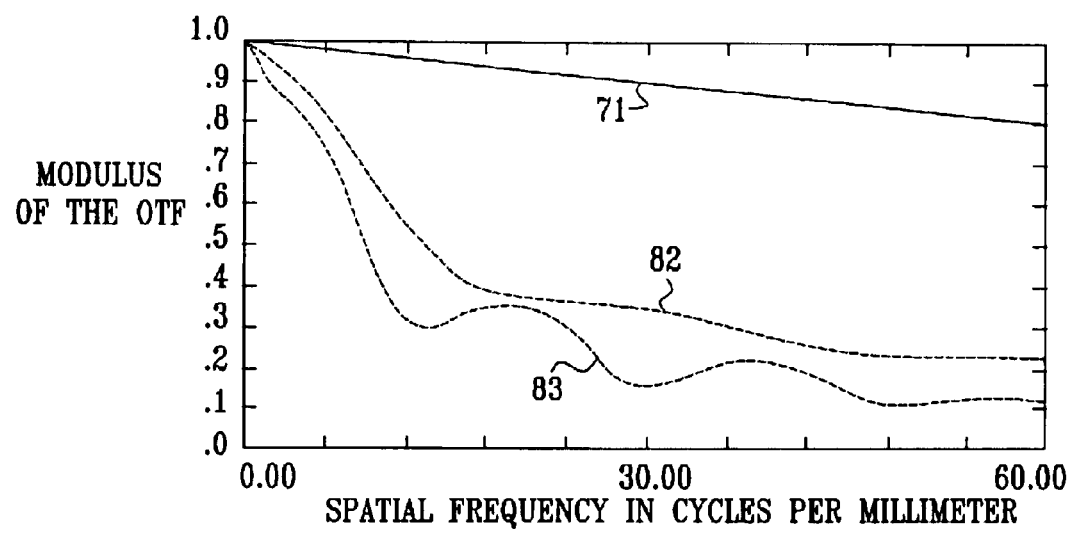
FIG. 10 shows MTF plots of an eye, whose vision has been corrected by means of the same spectacle lens as is used to provide the results shown in FIG. 9, but wherein the lens is tilted by an angle of 10° from the on-axis case.

Reference is now made to FIG. 10, which illustrates this effect of tilt. FIG. 10 is an MTF plot of an eye, whose vision has been corrected by means of the same spectacle lens as is used to provide the on-axis visual image quality shown in FIG. 9, but wherein the lens is tilted relative to the eye by an angle of 10° from the on-axis case. The curves 82 and 83 show the MTF obtained at the limits of the tilt used, ±10°. As is observed, the MTF decays from the on-axis case, but is still similar to that provided by the prior art, low order aberration correction lens, as shown in FIG. 8, or that provided by a standard healthy eye. This lens can thus be summarized as giving close to optimum super vision for on-axis vision, without an unreasonable decay of correction when the eye is rolled.

If however, the optimization procedure were to be performed over the selected range of angles of tilt, using a higher tilt weighting factor, and a lower field of view weighting factor, the lens performance could be modified to provide better acuity at higher tilt conditions than those shown in FIG. 10

Figure 11:
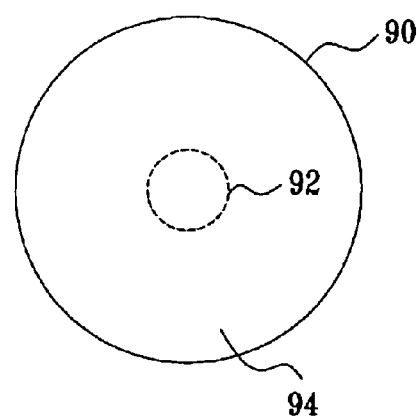
FIG. 11 is a schematic view of a spectacle lens, constructed and operative according to another preferred embodiment of the present invention, in which the lens is divided into two areas, a central area and an outer area.

Reference is now made to FIG. 11, which is a schematic view of a spectacle lens 90, constructed and operative according to another preferred embodiment of the present invention, in which the lens is divided into two areas, a central area 92, covering a field of view of ±1° when the spectacles are worn correctly, and an outer area 94. In the central area, the lens is designed to provide optimum paraxial high order aberration correction, such as that shown in FIG. 9. In the outer area 94 of the lens, correction is applied only for low order aberrations, such as defocus and astigmatism, such prior art corrections being more tolerant of angular tilt than the high order aberration correction of the central area 92. As a result, when the user's eye is directed paraxially through the central area of the lens, the optimum level of super vision is obtained, whereas when the user rolls his eye to look at an angle to the optical axis of the lens, he observes a conventionally corrected image, such as is obtained using currently available spectacle lenses. A smooth transition is preferably arranged between the two areas of the lens, to provide a natural image. Such an embodiment can be effectively described in terms of the weighting factors, wherein the FoV weighting factor is made very sharp, almost resembling a step function.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

What is claimed is:

1. A method of correcting aberrations in the vision of a subject, comprising the steps of:
   measuring said aberrations at an eye of said subject;
   providing a correction lens; and
   performing a simultaneous optimization over a range of vision angles, of parameters of said correction lens, such that a total averaged residual aberration over said range of vision angles of said eye and said correction lens is minimized.

2. The method of claim 1 wherein said parameters of said lens comprise at least one of a first surface, a second surface, and a thickness.

3. The method of claim 1 wherein said aberrations comprise high order aberrations.

4. The method of claim 1 wherein said correction lens is selected from a group consisting of a contact lens and an intraocular lens.

5. The method of claim 1 wherein said correction lens is a spectacle lens.

6. The method of claim 5 wherein said vision angles comprise angles of tilt of the axis of said eye relative to said lens.

7. The method of claim 5 wherein said vision angles comprise angles of tilt of the axis of said eye relative to said lens, and angles of off-axis vision of said eye.

8. The method of claim 5 wherein said optimization of the parameters of said lens comprises the steps of:
   calculating a first modulation transfer function of a combination of said lens and said eye for a given angle of tilt and a given angle of off-axis vision of said eye;
   varying at least one of said angle of tilt and said angle of off-axis vision over a predetermined range of angles;
   calculating new modulation transfer functions for said range of angles;
   performing a summation of said calculated modulation transfer functions; and
   varying said parameters of said lens to optimize said summation of said modulation transfer functions.

9. The method of claim 8, and wherein said step of optimizing said parameters of said correction lens over a range of vision angles is performed over a predetermined range of spatial frequencies.

10. The method of claim 8 and also comprising the step of applying a predefined weighting to each of said new modulation transfer functions for each of said vision angles before said summation of said calculated modulation transfer functions is performed.

11. The method of claim 10 wherein said predefined weighting is a function of said angle of tilt of said axis of said eye relative to said lens.

12. The method of claim 10 wherein said predefined weighting is a function of said angle of off-axis vision within a predefined field of view of said eye.

13. The method of claim 5 wherein said measuring said aberrations at an eye of said subject comprises the step of measuring a wavefront emitted from said subject's eye.

14. The method of claim 13 wherein said step of calculating a modulation transfer function of said combination of said lens and said eye is performed by calculating the effect of the passage of said wavefront through said lens.

15. The method of claim 1 wherein said vision angles comprise angles of off-axis vision of said eye.

16. The method of claim 1 wherein said optimization of the parameters of said lens comprises the steps of:
   calculating a first modulation transfer function of a combination of said lens and said eye for a given vision angle of said eye;
   varying said vision angle over a predefined range of angles;
   calculating new modulation transfer functions for each of a plurality of vision angles within said range of angles;
   performing a summation of said calculated modulation transfer functions; and
   varying said parameters of said lens to optimize said summation of said modulation transfer functions.

17. The method of claim 16, and wherein said step of optimizing said parameters of said correction lens over a range of vision angles is performed over a predetermined range of spatial frequencies.

18. The method of claim 16 and also comprising the step of applying a predefined weighting to each of said new modulation transfer functions for each of said vision angles before said summation of said calculated modulation transfer functions is performed.

19. The method of claim 18 wherein said vision angles comprise angles of tilt of said axis of said eye relative to said lens, and wherein said predefined weighting is a function of said angles of tilt of said axis of said eye relative to said lens.

20. The method of claim 18 wherein said vision angles comprise angles of off-axis vision of said eye, and wherein said predefined weighting is a function of said angles of off-axis vision within a predefined field of view of said eye.

21. The method of claim 1 wherein said measuring said aberrations at an eye of said subject comprises the step of measuring a wavefront emitted from said subject's eye.

22. The method of claim 21 wherein said step of calculating a modulation transfer function of said combination of said lens and said eye is performed by calculating the effect of the passage of said wavefront through said lens.

23. The method of claim 21 wherein said optimization of the parameters of said lens comprises the steps of:
calculating the deviation of said wavefront from a plane wavefront after passage through said combination of said lens and said eye, for a given vision angle of said eye;
varying said vision angle over a predefined range of angles;
calculating a new deviation of said wavefront for each of a plurality of vision angles within said range of angles;
summing said calculated deviations of said wavefront; and
varying said parameters of said lens to minimize said sum of said deviations of said wavefront from a plane wavefront.

24. The method of claim 23 and also comprising the step of applying a predefined weighting to each of said new calculated deviations of said wavefront for each of said vision angles before said summation of said calculated deviations is performed.

25. The method of claim 24 wherein said vision angles comprise angles of tilt of said axis of said eye relative to said lens, and wherein said predefined weighting is a function of said angles of tilt of said axis of said eye relative to said lens.

26. The method of claim 24 wherein said vision angles comprise angles of off-axis vision of said eye, and wherein said predefined weighting is a function of said angles of off-axis vision within a predefined field of view of said eye.

27. The method of claim 21 wherein said optimization of the parameters of said lens comprises the steps of:
calculating the deviation of said wavefront from a plane wavefront after passage through said combination of said lens and said eye, for a given angle of tilt and a given angle of off-axis vision of said eye;
varying at least one of said angle of tilt and said angle of off-axis vision over a predetermined range of angles;
calculating a new deviation of said wavefront for each of a plurality of vision angles within said range of angles;
summing said calculated deviations of said wavefront; and
varying said parameters of said lens to minimize said sum of said deviations of said wavefront from a plane wavefront.

28. The method of claim 27 and also comprising the step of applying a predefined weighting to each of said new calculated deviations of said wavefront for each of said vision angles before said summation of said calculated deviations is performed.

29. The method of claim 28 wherein said predefined weighting is a function of said angle of tilt of said axis of said eye relative to said lens.

30. The method of claim 28 wherein said predefined weighting is a function of said angle of off-axis vision within a predefined field of view of said eye.

31. A method of correcting aberrations in the vision of a subject, comprising the steps of:
measuring said aberrations at an eye of said subject, said eye having a cornea;
measuring the profile of the front surface of said cornea of said eye;
optimizing over a range of angles of off-axis vision within a predetermined field of view of said eye, the front surface of said cornea, such that a total averaged residual aberration over said range of angles of off-axis vision within said predetermined field of view of said eye is minimized; and
performing refractive surgery on said eye such that said cornea acquires said optimized front surface.

32. The method according to claim 31 wherein said aberrations comprise high order aberrations.

33. The method of claim 31 wherein said optimization of the front surface of said cornea comprises the steps of:
calculating a first modulation transfer function of said eye with said front surface for a given angle of off-axis vision of said eye;
varying said angle of off-axis vision over a predefined range of angles;
calculating new modulation transfer functions for each of a plurality of angles of off-axis vision within said range of angles;
performing a summation of said calculated modulation transfer functions; and
varying said front surface of said cornea to optimize said summation of said modulation transfer functions.

34. The method of claim 33 and also comprising the step of applying a predefined weighting to each of said new modulation transfer functions for each of said angles of off-axis vision before said summation of said calculated modulation transfer functions is performed.

35. The method of claim 34 wherein said predefined weighting is a function of said angle of off-axis vision within a predefined field of view of said eye.

36. The method of claim 31, and wherein said step of optimizing said front surface of said cornea over a range of angles of off-axis vision is performed over a predetermined range of spatial frequencies.

37. The method of claim 31, wherein said measuring said aberrations at an eye of said subject comprises the step of measuring a wavefront emitted from said subject's eye.

38. The method of claim 37 wherein said optimization of the front surface of said cornea comprises the steps of:
calculating the deviation of said wavefront from a plane wavefront after passage through said eye with said cornea front surface, for a given angle of off-axis vision of said eye;
varying said angle of off-axis vision over a predetermined range of angles;
calculating a new deviation of said wavefront for each of a plurality of vision angles within said range of angles;
summing said calculated deviations of said wavefront; and
varying said front surface of said cornea to minimize said sum of said deviations of said wavefront from a plane wavefront.

* * * * *